United States Patent [19]

Greenwald

[11] 4,009,167
[45] Feb. 22, 1977

[54] N-(LOWER ALKYL SULFONYL-METHYL SULFONYL)-PIPERAZINES

[75] Inventor: Richard B. Greenwald, Lexington, Mass.

[73] Assignee: Polaroid Corporation, Cambridge, Mass.

[22] Filed: Apr. 29, 1976

[21] Appl. No.: 681,583

Related U.S. Application Data

[63] Continuation-in-part of Ser. No. 564,166, April 1, 1975, Pat. No. 3,976,647.

[52] U.S. Cl. .............................. 260/268 S; 96/29 R
[51] Int. Cl.² ................................. C07D 295/20
[58] Field of Search ........................ 260/268 S

[56] References Cited
UNITED STATES PATENTS 3,836,535   9/1974   Shun-Ichi Naito ............. 260/268 S
3,895,010   7/1975   Goralski et al. .............. 260/268 S Primary Examiner—Donald G. Daus
Assistant Examiner—Jose Tovar
Attorney, Agent, or Firm—Sybil A. Campbell

[57] ABSTRACT

This application is directed to compounds of the formula

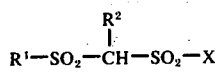

wherein $R^1$ is lower alkyl; $R^2$ is hydrogen, lower alkyl or $-(CH_2)_m S-(CH_2)_n Y$ wherein $m$ is a whole number 2 to 5, $n$ is a whole number 1 to 4 and Y is hydrogen, —OH or —COOR wherein R is hydrogen or lower alkyl; and X is

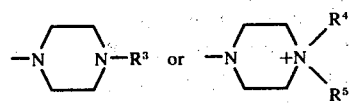

wherein A is a halide or sulfonate, $R^3$ is hydrogen or $-(CH_2)_n Y$ wherein $n$ and Y have the same meaning given above, $R^4$ is $-(CH_2)_n Y$ wherein $n$ and Y have the same meaning given above and $R^5$ is lower alkyl. These compounds are useful as silver halide solvents in photography.

12 Claims, No Drawings

N-(LOWER ALKYL SULFONYL-METHYL SULFONYL)-PIPERAZINES

CROSS-REFERENCE TO RELATED PATENT APPLICATIONS

This application is a continuation-in-part of my copending application Ser. No. 564,166 filed Apr. 1, 1975, now U.S. Pat. No. 3,976,647 issued 8/24/76.

BACKGROUND OF THE INVENTION

1. Field of the Invention

This invention relates to novel chemical compounds useful as silver halide solvents in photography.

2. Description of the Prior Art

Photographic processing compositions capable of forming water-soluble complex silver salts are known to be useful in many types of silver halide photography. To obtain a relatively stable image in an exposed and developed photosensitive silver halide emulsion, the silver halide remaining in the unexposed and undeveloped areas of the emulsion should be converted to a soluble silver complex that can be removed by washing or converted to a stable silver complex that will not "print-out" upon prolonged exposure to light. In conventional or "tray" development, it is customary to fix the developed silver halide emulsion by applying a solution of silver halide solvent, i.e., silver halide complexing agent which forms a water-soluble silver complex with the residual silver halide. The water-soluble silver complex thus formed and excess silver halide solvent are then removed from the developed and fixed emulsion by washing with water.

Silver halide solvents also have been employed in monobaths where a single processing composition containing a silver halide developing agent in addition to the silver halide solvent is utilized for both developing and fixing an exposed photosensitive silver halide layer. Silver halide solvents also have been employed in diffusion transfer photographic processes. Such processes are now well known in the art; see for example, U.S. Pat. Nos. 2,543,181; 2,647,056; 2,983,606; etc. In processes of this type, an exposed silver halide emulsion is treated with a processing composition whereby the exposed silver halide emulsion is developed and an imagewise distribution of diffusible image-forming components is formed in the unexposed and undeveloped portions of the silver halide emulsion. This distribution of image-forming components is transferred by imbibition to an image-receiving stratum in superposed relationship with the silver halide emulsion to provide the desired transfer image. In diffusion transfer processes where a silver transfer image is formed, processing is effected in the presence of a silver halide solvent which forms a diffusible complex with the undeveloped silver halide. The soluble silver complex thus formed diffuses to the superposed image-receiving layer where the transferred silver ions are deposited as metallic silver to provide the silver transfer image. In preparing silver prints in this manner, the image-receiving element preferably includes a silver precipitating agent, for example, heavy metal sulfides and selenides as described in U.S. Pat. No. 2,698,237 of Edwin H. Land.

Various compounds have been employed as silver halide solvents in the photographic processes described above. One of the most commonly employed is sodium thiosulfate. Other silver halide solvents that have been used include thiocyanates, such as potassium and sodium thiocyanate; and cyclic imides, such as barbituric acid and uracil. U.S. Pat. No. 3,769,014 discloses still another class of silver halide solvents, namely, 1,1-bis-sulfonyl alkanes.

The present invention is concerned with novel compounds useful as silver halide solvents in both conventional and diffusion transfer photography.

SUMMARY OF THE INVENTION

It is the primary object of the present invention to provide certain chemical compounds as set forth hereinafter.

It is a further object of the present invention to provide novel chemical compounds useful for complexing silver ion, i.e., undeveloped silver halide in photographic processes.

Other objects of this invention will in part be obvious and will in part appear hereinafter.

The invention accordingly comprises the products and compositions possessing the features, properties and the relation of elements which are exemplified in the following detailed disclosure, and the scope of the application of which will be indicated in the claims.

For a fuller understanding of the nature and objects of the invention, reference should be had to the following detailed description.

DETAILED DESCRIPTION OF THE INVENTION

The novel compounds of this invention may be represented by the formula

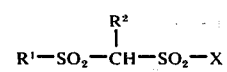

wherein $R^1$ is lower alkyl; $R^2$ is hydrogen, lower alkyl or $-(CH_2)_m S-(CH_2)_n-Y$ wherein $m$ is a whole number 2 to 5, $n$ is a whole number 1 to 4 and Y is hydrogen, $-OH$ or $-COOR$ wherein R is hydrogen or lower alkyl; and X is

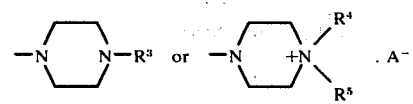

wherein A is a halide or a sulfonate, $R^3$ is hydrogen or $-(CH_2)_n-Y$ wherein $n$ and Y have the same meaning given above, $R^4$ is $-(CH_2)_n-Y$ wherein $n$ and Y have the same meaning given above and $R^5$ is lower alkyl. In a preferred embodiment, $R^2$ is hydrogen or $-(CH_2)_m-S-(CH_2)_n-Y$, $m$ is 2 or 3, $n$ is 1 or 2, and $R^3$ is $-(CH_2)_n-Y$. In the quaternized compounds, the Y of the $R^4$ substituent preferably is H and $R^4$ and $R^5$ preferably are the same.

As used herein, the term "lower alkyl" is intended to mean alkyl groups containing one to four carbon atoms, for example, methyl, ethyl, propyl, isopropyl, s-butyl and n-butyl.

Specific examples of compounds within the scope of the present invention are as follows:

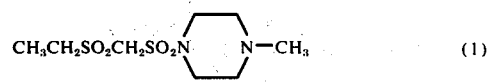
(1)

-continued

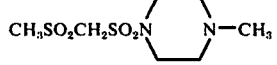 (2)

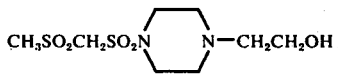 (3)

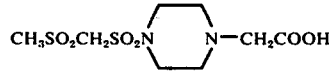 (4)

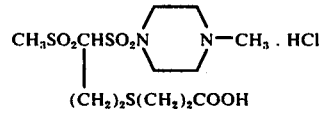 (5)

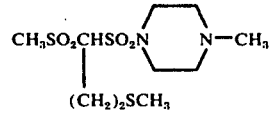 (6)

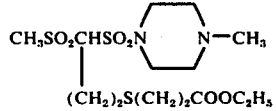 (7)

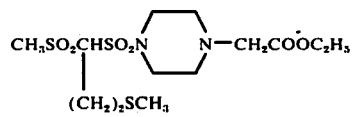 (8)

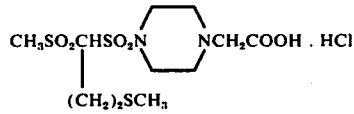 (9)

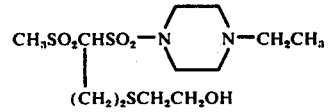 (10)

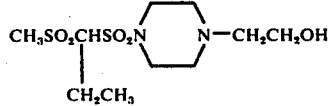 (11)

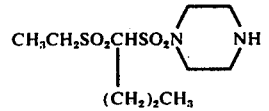 (12)

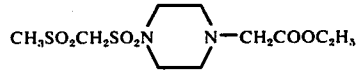 (13)

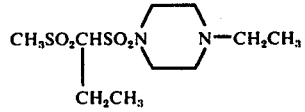 (14)

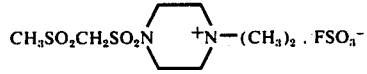 (15)

-continued

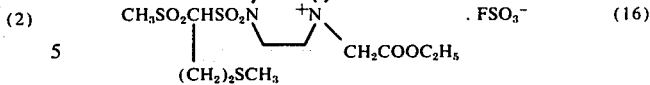 (16)

In preparing the non-quaternized compounds, the non-S-substituted compounds may be conveniently synthesized, for example, by reacting a sulfene with the selected piperazine in accordance with the procedure described by G. Opitz et al., Angew. Chem. Internat. Edit., Vol. 5 (1966), p. 594–5. The compounds substituted with the —S-containing moiety may be prepared, for example, by reacting the non-S-substituted sulfonylsulfonamido alkanes with the chloro-substituted derivative of the selected $R^2$ substituent, i.e., Y-(-CH$_2$)-$_n$S-(-CH$_2$-)$_m$Cl. The quaternized compounds may be synthesized by reacting the non-S-substituted or S-substituted compounds usually as a tertiary amine, i.e., $R^3$ is other than hydrogen with an alkyl halide or sulfonate.

The following examples are given to further illustrate the present invention and are not intended to limit the scope thereof.

EXAMPLE 1

Preparation of the compound having the formula

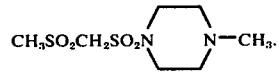

A solution of triethylamine (31 g., 300 mmoles) in 200 mls of acetonitrile was chilled in dry ice/alcohol to about −50° C. Methanesulfonylchloride (23 g., 200 mmoles) was added dropwise to the cooled solution over 10 minutes with stirring. Stirring was continued for 20 minutes, and N-methylpiperazine (10 g., 100 mmoles) was added over 10 minutes. The reaction mixture was allowed to stand for about 2 days at room temperature and then stripped on a rotovac. The residue was triturated with water and the title compound collected (15.3 g., melting range 195°–198° C.)

EXAMPLE 2

Preparation of the compound having the formula

The procedure of Example 1 was repeated using 44 g. of triethylamine in 450 mls. of acetonitrile, 25 g. of 1-piperazine acetic acid ethylester and 33.2 g. of methanesulfonylchloride. The title compound was collected as a white solid (44.2 g., melting range 215°–216° C.).

EXAMPLE 3

Preparation of the compound having the formula

The procedure of Example 1 was repeated using 30.3 g. of triethylamine in 200 mls. of acetonitrile, 13 g. of N-(2-hydroxyethyl)piperazine in 10 mls. of tetrahydrofuran and 23 g. of methanesulfonylchloride. The crude product was collected and recrystallized from boiling ethanol yielding about 3 g. of the title compound (melting range 117°–119° C.).

EXAMPLE 4

Preparation of the compound having the formula

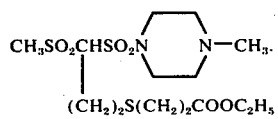

The compound of Example 1 (5g., 19.4 mmoles) was dissolved in N,N-dimethylformamide by heating to 60° C. Sodium hydride (57% by weight dispersion in oil; 1 g.) was added to the solution and the mixture heated at about 70° C. for 1.25 hours. The chloride, Cl—$(CH_2)_2S(CH_2)_2CO_2C_2H_5$, (4.6 g., 23.3 mmoles) was then added over 15 minutes and the reaction mixture heated to 100° C. Heating at about 85° C. was continued overnight and then the reaction mixture was heated at 105° C. for about 2 hours. After cooling, the mixture was poured onto ice, and the filtrate decanted from a tacky gray solid. the remaining filtrate was stripped on a rotovac and the residue taken up in 50 mls. ethanol. A white solid (1.2 g.) was collected by filtration and the filtrate stripped to give a sticky white solid (4.8 g.) which was triturated briefly with ether. The title compound was separated from the white solid by chromatography using about 100 g. of silica gel which was eluted with chloroform, 2% methanol and 5% methanol in 200 ml fractions. Fraction 6 contained about 1.4 g. of the title compound, essentially homogeneous by NMR (> 95% purity, melting range 124°–126° C.)

EXAMPLE 5

Preparation of the compound having the formula

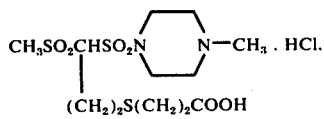

The compound of Example 4 (1.2 g., 2.9 mmoles) was dissolved in 25 mls. of 6N hydrochloric acid and heated at reflux for 2.5 hours. The solution was allowed to stand overnight at room temperature and then stripped on a rotovac yielding the title compound as a white powder (1.1 g., melting point about 100° C.)

EXAMPLE 6

Preparation of the compound having the formula

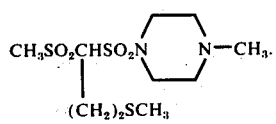

The procedure of Example 4 was repeated using 4.5 g. of the compound of Example 1 in 25 mls. of N,N-dimethylformamide, 0.75 g. of 57% sodium hydride and 1.92 g. of chloroethylmethylsulfide except that the reaction mixture after being poured over ice was adjusted to a pH of about 7 with approximately 0.5 ml. of hydrochloric acid, filtered after the addition of Celite, and stripped to give a semisolid amber syrup which was triturated with several portions of ether to give a solid ball essentially insoluble in ethylacetate. The solid was partitioned between ethylacetate/water and the ethylacetate dried and stripped to give an amber liquid which crystallized on standing overnight. After triturating with ether, the title compound was collected (0.75 g.).

EXAMPLE 7

Preparation of the compound having the formula

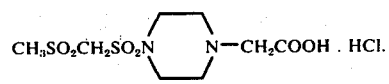

The compound of Example 2 (2. g., 6.1 mmoles) was dissolved in 12 mls of 3N hydrochloric acid by heating. Heating on a steam bath was continued overnight and then the solution was filtered to remove insolubles and stripped on a rotovac to give the title compound as a white solid (1.7 g., melting range 338°–340° C. dec.).

EXAMPLE 8

Preparation of the compound having the formula

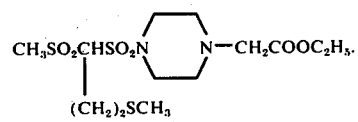

The procedure of Example 4 was repeated using 7 g. of the compound of Example 2 in 50 mls. of N,N-dimethylformamide, 0.9 g. of 57% sodium hydride and 2.35 g. of chloroethylmethylsulfide except that the reaction mixture after being poured over ice was adjusted to a pH of about 7 with hydrochloric acid and allowed to stand for about one hour. The crystalline precipitate that formed on standing was washed with water and triturated with ether to give 4 g. of the title compound (melting range 57°–60° C.).

EXAMPLE 9

Preparation of the compound having the formula

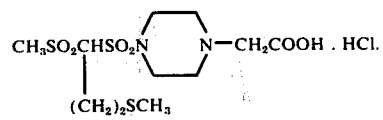

The compound of Example 8 (1.5 g.) was taken up in 20 mls. of 3N hydrochloric acid and heated on a steam bath overnight. After the addition of Celite, the solution was filtered and stripped on a rotovac leaving a brittle foam which upon standing for several days gave a glass. The glass was taken up in water to give a 50% aqueous solution. After standing for several days, a tan solid crystallized which was collected to give 0.5 g. of the title compound (melting range 196°–198° C. dec.).

EXAMPLE 10

Preparation of the compound having the formula

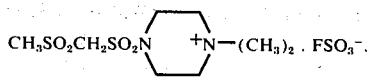

The compound of Example 1 (1.25 g., 4.9 mmoles) was dissolved in 25 mls of acetonitrile by warming and the solution allowed to cool to room temperature. Methylfulorosulfonate (0.56 g., 4.9 mmoles) was added to the cooled solution and the reaction mixture was warmed briefly. A white solid separated, and after about 15 minutes when the reaction mixture had cooled to room temperature, the white solid was collected to give 1.4 g. of the title compound.

EXAMPLE 11

Preparation of the compound having the formula

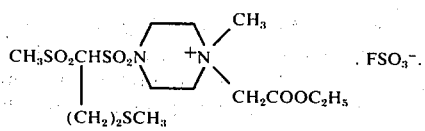

The procedure of Example 10 was repeated except that the compound of Example 8 was reacted with methylfluorosulfonate to give the title compound.

As noted above, the compounds of the present invention are broadly useful in a variety of photographic processes of the type in which water-soluble silver complexes are formed from the unreduced silver halide of a photoexposed and at least partially developed silver halide stratum including both conventional and diffusion transfer photographic processes. The photographic use of these compounds as silver halide solvents in photographic processes forms the subject matter of copending U.S. patent application Ser. No. 564,167 of Richard B. Greenwald filed concurrently herewith. For convenience, the specification of said application is specifically incorporated herein.

To illustrate the utility of the above-defined compounds as photographic silver halide solvents, a photosensitive silver halide emulsion on a support was exposed to a step wedge and processed by spreading a layer of processing composition approximately 1.2 mils. thick between the exposed emulsion and a superposed image-receiving element comprising a layer of regenerated cellulose containing colloidal palladium sulfide carried on a transparent support. The processing composition was prepared by adding a compound of the present invention in a concentration of 5% by weight to the following formulation:

| Water | 814.0 g. |
|---|---|
| Potassium hydroxide (Aqueous 50% w/w solution) | 348.0 g. |
| Hydroxyethyl cellulose | 35.0 g. |
| Zinc acetate | 15.0 g. |
| Triethanolamine Bis-N,N-methoxyethyl | 5.6 g. |
| hydroxylamine | 50.0 g. |

After an imbibition period of approximately one minute, the developed silver halide emulsion was separated from the image-receiving element, and the maximum and minimum transmission densities were measured for the positive image.

The compounds added to the base formulation as silver halide solvents, and the density measurements for the positive image obtained with each of the compounds are set forth in the following table:

TABLE

| Compound | Density | |
| (Formula No.) | Maximum | Minimum |
|---|---|---|
| (2) | 2.32 | 0.26 |
| (3) | 1.70 | 0.09 |
| (4) | 1.67 | 0.08 |
| (15) | 0.98 | 0.30 |

The compounds of the present invention have been found to give higher maximum densities than the corresponding compound with other heterocyclic groups in place of the 1-piperizinyl group. For example, the foregoing procedure was repeated using

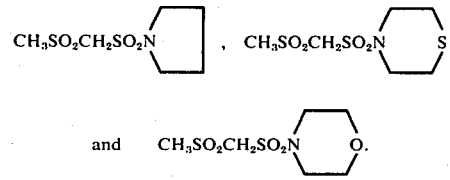

and 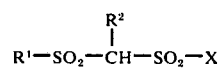

The density measurements for the positive image obtained, i.e., $D_{max}/D_{min}$ were 0.55/0.07, 0.08/0.02 and 0.49/0.06, respectively.

Since certain changes may be made in the above composition and processes without departing from the scope of the invention herein involved, it is intended that all matter contained in the above description should be interpreted as illustrative and not in a limiting sense.

What is claimed is:

1. A compound of the formula:

$$R^1-SO_2-\overset{\overset{R^2}{|}}{C}H-SO_2-X$$

wherein $R^1$ is lower alkyl; $R^2$ is $-(CH_2)_m S-(CH_2)_n Y$ wherein $m$ is a whole number 2 to 5, $n$ is a whole number 1 to 4 and Y is hydrogen, —OH or —COOR wherein R is hydrogen or lower alkyl; and X is

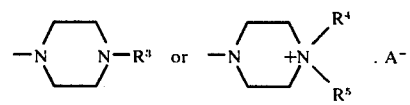

wherein A is a halide or a sulfonate, $R^3$ is hydrogen or $-(CH_2)_n Y$ wherein $n$ and Y have the same meaning given above, $R^4$ is $-(CH_2)_n Y$ wherein $n$ and Y have the same meaning given above and $R^5$ is lower alkyl.

2. A compound as defined in claim 1 wherein X is

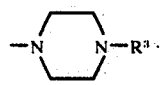

3. A compound as defined in claim 1 wherein X is

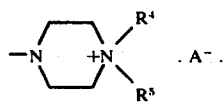

4. A compound as defined in claim 2 wherein $R^3$ is $-(CH_2)_m-Y$.

5. A compound as defined in claim 3 wherein said Y of said $R^4$ is $-COOR$.

6. A compound as defined in claim 1 wherein said $m$ is 2.

7. The compound having the formula

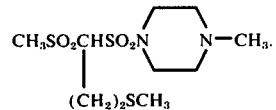

8. The compound having the formula

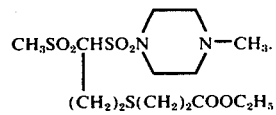

9. The compound having the formula

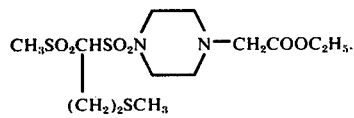

10. The compound having the formula

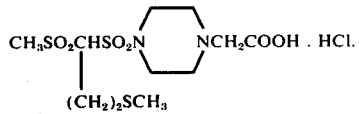

11. The compound having the formula $$CH_3SO_2CHSO_2N\text{—piperazine—}NCH_2COOH \cdot HCl$$
with $(CH_2)_2SCH_3$ substituent.

12. The compound having the formula

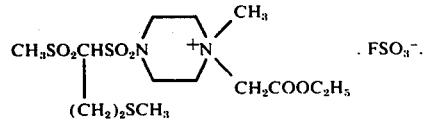

* * * * *